(12) United States Patent
Mueller

(10) Patent No.: US 9,365,304 B2
(45) Date of Patent: Jun. 14, 2016

(54) CONTAINER ARRANGEMENT AND METHOD FOR FILLING FLEXIBLE DISPOSABLE BAGS

(71) Applicant: Sartorius Lab Instruments GmbH & Co. KG, Goettingen (DE)

(72) Inventor: Michael Mueller, Goettingen (DE)

(73) Assignee: Sartorius Lab Instruments GmbH & Co. KG, Goettingen (DE)

(*) Notice: Subject to any disclaimer, the term of this patent is extended or adjusted under 35 U.S.C. 154(b) by 417 days.

(21) Appl. No.: 13/891,887

(22) Filed: May 10, 2013

(65) Prior Publication Data

US 2013/0240082 A1 Sep. 19, 2013

Related U.S. Application Data

(63) Continuation of application No. PCT/EP2011/003786, filed on Jul. 27, 2011.

(30) Foreign Application Priority Data

Nov. 10, 2010 (DE) .................. 10 2010 060 469

(51) Int. Cl.
| | |
|---|---|
| B65B 3/04 | (2006.01) |
| B65B 3/00 | (2006.01) |
| F16K 7/04 | (2006.01) |
| F16K 15/04 | (2006.01) |
| A61M 1/02 | (2006.01) |
| B65B 3/28 | (2006.01) |

(52) U.S. Cl.
CPC ................ *B65B 3/04* (2013.01); *A61M 1/0231* (2014.02); *B65B 3/003* (2013.01); *F16K 7/04* (2013.01); *F16K 15/04* (2013.01); *B65B 3/28* (2013.01)

(58) Field of Classification Search
CPC ........ B65B 3/04; B65B 3/003; A61M 1/0231
USPC ...................... 141/10, 99, 237–244
See application file for complete search history.

(56) References Cited

U.S. PATENT DOCUMENTS

| | | | |
|---|---|---|---|
| 3,430,648 A | | 3/1969 | Botkin |
| 3,566,930 A | * | 3/1971 | Kirschner ................. 141/244 |
| 4,754,786 A | * | 7/1988 | Roberts ......................... 141/1 |
| 4,829,002 A | * | 5/1989 | Pattillo et al. ............ 435/297.1 |
| 4,964,261 A | * | 10/1990 | Benn ............................ 53/469 |
| 5,522,439 A | * | 6/1996 | Hakansson et al. ........... 141/244 |
| 5,701,937 A | * | 12/1997 | Bourboulou et al. ......... 141/244 |

(Continued)

FOREIGN PATENT DOCUMENTS

| | | |
|---|---|---|
| EP | 1693077 A2 | 8/2006 |
| EP | 1236644 B1 | 1/2007 |

(Continued)

*Primary Examiner* — Timothy L Maust
(74) *Attorney, Agent, or Firm* — Edell, Shapiro & Finnan, LLC

(57) ABSTRACT

A container arrangement includes a plurality of flexible disposable bags (20a, b, c) which each have an inlet element to which a flexible connecting tube (18a, b, c) is attached, wherein each connecting tube (18a, b, c) branches off from a flexible common main line (12, 14, 16) which has a common inlet section (12) on the intake end. The main line (12, 14, 16) has a common gas outlet section (14) at the discharge end. A non-return valve (146) which closes against the gas outlet direction and a gas-permeable, liquid-tight sterile filter (144) are arranged in the common gas outlet section.

14 Claims, 1 Drawing Sheet

(56) References Cited

U.S. PATENT DOCUMENTS

| | | | |
|---|---|---|---|
| 5,819,816 A * | 10/1998 | Mayer | 141/83 |
| 6,024,251 A * | 2/2000 | Mayer et al. | 222/64 |
| 6,450,215 B1 * | 9/2002 | Willemstyn et al. | 141/10 |
| 6,725,888 B1 | 4/2004 | Richter et al. | |
| 7,461,671 B2 * | 12/2008 | Ehwald et al. | 141/244 |
| 2005/0109795 A1 | 5/2005 | Furey et al. | |
| 2010/0236340 A1 | 9/2010 | Lee et al. | |
| 2013/0220484 A1 * | 8/2013 | De Marco | 141/183 |
| 2014/0027010 A1 * | 1/2014 | Janssens et al. | 141/5 |
| 2014/0137519 A1 * | 5/2014 | Goodwin et al. | 53/456 |

FOREIGN PATENT DOCUMENTS

| | | |
|---|---|---|
| EP | 1525138 B1 | 12/2008 |
| WO | 9309863 A1 | 5/1993 |
| WO | 03106266 A1 | 12/2003 |
| WO | WO 2012092394 A1 * | 7/2012 |

* cited by examiner

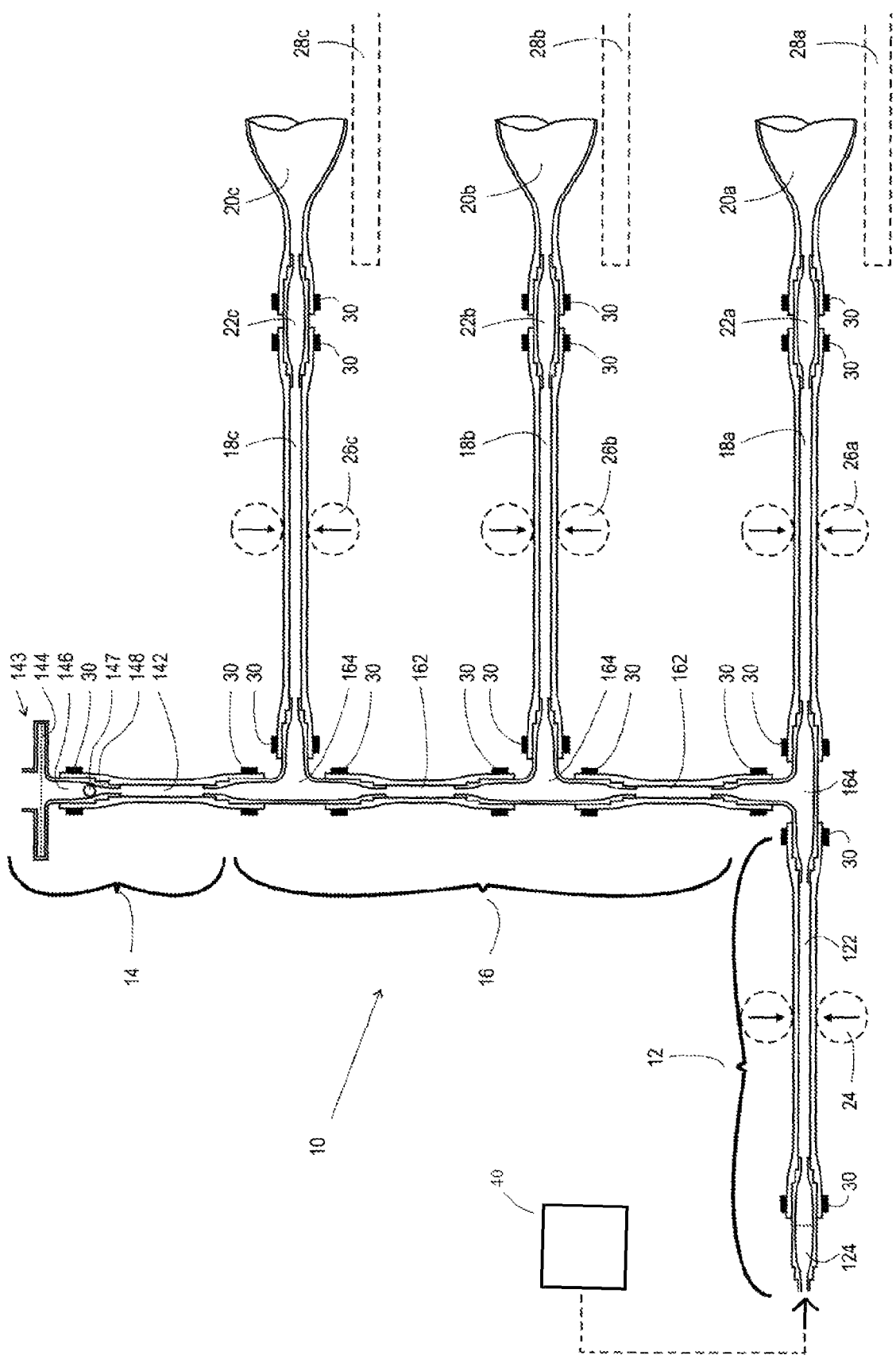

CONTAINER ARRANGEMENT AND METHOD FOR FILLING FLEXIBLE DISPOSABLE BAGS

The present application is a Bypass Continuation of International Application No. PCT/EP2011/003786, filed on Jul. 27, 2011, which claims priority from German Patent Application 10 2010 060 469.0, filed on Nov. 10, 2010. The contents of these prior applications are hereby incorporated by reference in their respective entireties into the present application.

FIELD AND BACKGROUND OF THE INVENTION

The invention relates to a container arrangement comprising a plurality of flexible disposable bags, each of which has an inlet element, to which a flexible connecting tube is attached, wherein each connecting tube branches off from a flexible common main line, which has a common inlet section at the input end.

Furthermore, the invention relates to a method for filling the flexible disposable bags of such a container arrangement.

A container arrangement of this type is known from EP 1 525 138 B1. Such container arrangements follow the common trend in medical technology and biotechnology away from reusable containers to disposable containers that are designed to be used once and then disposed. The containers are constructed as flexible plastic bags with at least one inlet element. Each bag is attached to a main line via a flexible connecting tube that is assigned to each bag, and this main line is usually constructed as a flexible tube. The main line has an inlet section at the input end. The inlet section can be attached, for example, to a pump. It is well known that such container arrangements are marketed as prefabricated, sterile units. Their use takes place in a filling system, which has a plurality of pinch valves, wherein each connecting tube is inserted into an assigned pinch valve. The inlet section of the main line is attached to a pump that is connected to a supply container. It is also known to connect the inlet section of the main line directly to the supply container or to a cutoff valve that is assigned to that supply container. In this case the supply container is either pressurized per se or is positioned higher than the disposable bags that serve as the target bags in the container arrangement. The target bags can be filled one after the other from the supply container by opening the pinch valves individually in an alternating fashion. Preferably, at the same time the fill level of the target bags is monitored, for example, gravimetrically. The drawback with the known system is the lack of a degassing possibility for expelling the residual gas in the tubing system prior to filling the disposable bags. The result is that the residual gas is filled into at least one of the bags, a feature that is undesired in many cases.

EP 1 236 644 discloses a system for filling a target bag from a plurality of supply bags. All of the bags are connected to a common distributor through connecting tubes assigned to the respective bags. The distributor has a common central chamber, which has a plurality of inputs and outputs, each of which is closed by a switching valve. Each connecting tube is attached to such an input or output. A piston pump is connected to an additional input/output in the form of a typical injection syringe. A gas outlet nozzle, which is provided with a membrane filter, is connected to an additional input/output. In order to fill the bag, the piston of the piston pump is pulled back and pushed forward in phases; and at the same time the volume flow from the supply bags to the target bag is controlled by controlling the switching valves as required. The residual gas, which comes from the tubing system and which collects in the central chamber of the distributor, can be expelled by controlling, as required, the switching valve assigned to the gas outlet nozzle. A drawback with this arrangement is the technically intricate and, therefore, expensive configuration of the distributor that contains the switching valves. On the one hand, the distributor represents the central element of the tubing system, to which all of the connecting tubes have to be connected. On the other hand, the distributor cannot be constructed as a disposable element for cost reasons. Rather, the distributor is a reusable element that has to be cleaned and sterilized in a time-consuming and costly process after each usage. In other words, the typically sterile and prefabricated connecting tube-bag arrangements have to be coupled to a hygienically critical central element prior to each filling process, so that the coupling operation itself is also hygienically critical.

OBJECTS AND SUMMARY OF THE INVENTION

An object of the present invention is to provide a container arrangement of this type with a cost-effective degassing possibility and without having to accept hygienic drawbacks.

This engineering object is achieved with a container arrangement in which the main line has a common gas outlet section at the output end, at which a non-return valve, which closes against the gas outlet direction, and a gas permeable, liquid-impermeable sterile filter are arranged.

According to one aspect of the invention, the main line of the tubing system is provided with a gas outlet section at the output end. This means that the main line consists in essence of three sections: in particular, an inlet section and, connected thereto, a central section, from which the connecting tubes branch off in the direction of the individual disposable bags, and a gas outlet section that is connected to the central section. During a filling operation, when all of the connecting tubes are inserted into their assigned pinch valves and are closed by said pinch valves, this arrangement allows, first of all, the fluid to be introduced into the main line and the connecting tubes, which branch off from the main line (and from the connecting tubes to the respective blocking pinch valves) from a supply container, which is connected to the inlet section of the main line. At the same time this arrangement allows the residual gas, which may be found in the tubing system, to be pushed along the main line into the gas outlet section and through the gas permeable sterile filter to the external environment. The sterile filter is necessary, in order to prevent bacteria from being dragged in from the external environment into the tubing system, which at this point is open, according to the invention.

However, these measures alone would not be totally sufficient to achieve the engineering object. If, in particular, the pinch valve, which is assigned to the first disposable bag, were to be opened in order to fill the first disposable bag, there would be the risk that the priming fluid, i.e. the fluid that was pumped into the main line in order to drive out the residual gas, would be pressed into the open disposable bag. This risk would be especially high in cases in which the disposable bags to be filled are stacked one above the other, for example, in a stacking shelving system. The pressure of the liquid column over the branch of the disposable bag that has just been filled would push the fluid out of the main line and the connecting tube into the disposable bag. The result would be measurement errors, especially if the fill level were to be monitored gravimetrically. When the fill level is monitored gravimetrically, the entire system comprising disposable containers, connecting tubes and main line is arranged on a common weighing platform, so that gravimetrically it cannot be distinguished whether some of the fluid is in the main line or in a disposable bag.

Therefore, the invention also provides that, in addition, the gas outlet section has a non-return valve. This non-return valve is oriented in such a way that it allows a fluid stream in the gas outlet direction and blocks against the gas outlet direction. This arrangement prevents the priming fluid from flowing back into a disposable bag when the pinch valve associated with this disposable bag is opened. If the liquid column in the main line were to fall, the result would be a negative pressure at the non-return valve; and this negative pressure acts against the force of gravity and holds the liquid column in the main line. On the other hand, a fluid stream, which is, for example, driven by a pump and which flows from the supply container into the disposable bag, would be largely unaffected by the negative pressure at the non-return valve.

Preferably the non-return valve and the sterile filter are disposed in a common housing. That is, they are constructed as a common component or module. This measure helps to ensure the reliability during assembly and to optimize the installation space.

The arrangement of the non-return valve relative to the sterile filter can be carried out in different ways. A first embodiment provides that the non-return valve is arranged downstream of the sterile filter in the gas outlet direction and is constructed as a gas valve. As a result, the gas to be driven out passes first through the sterile filter and then through the non-return valve. In this arrangement the non-return valve does not make contact with the priming fluid at any time, because this priming fluid cannot pass through the fluid-tight sterile filter. Correspondingly the non-return valve should be constructed as a gas valve. That is, the non-return valve is constructed as a valve that is gas-tight in the closed state.

As explained above, the sterile filter marks the maximum fill height of the gas outlet section or more specifically the main line. This means that even in the event of maximum priming between the sterile filter and the non-return valve, a gas cushion is formed. Even if the liquid column in the main line falls due to the force of gravity when a pinch valve is opened, the non-return valve closes. However, owing to the compressibility of gases, the gas cushion expands at least slightly, so that the priming fluid cannot be held in its entirety in the main line, but rather some of the priming fluid (even if just a small portion) flows into the disposable bag. It is possible to compensate for the resulting error in the amount filled into the bag (since the amount of error can be easily determined in tests) by filling the disposable bag with a correspondingly smaller amount. Furthermore, the error can be reduced by decreasing the distance between the sterile filter and the non-return valve and, thus, minimizing the gas cushion.

Such a filling error is almost completely avoided in an alternative embodiment, which provides that the non-return valve is arranged upstream of the sterile filter in the gas outlet direction and is constructed as a fluid valve. Given maximum priming, i.e. when priming up to the sterile filter, the non-return valve is traversed by the priming fluid. As a result, the non-return valve has to be constructed as a fluid valve, i.e. as a valve that is capable of blocking in a fluid-tight manner.

In this embodiment a gas cushion must not be generated upstream of the non-return valve when the priming is adequately high. Due to the extremely small compressibility of fluids, the liquid column in the main line does not sink for all practical purposes when the pinch valve, assigned to the disposable bag, is opened. The resulting filling error can be ignored.

In this embodiment the contact between the inner elements of the non-return valve and the priming fluid can present a problem. Typical non-return valves are made of metal materials that under some circumstances can react in an undesired way to sensitive biotechnological fluids. In order to prevent such a reaction, a further development of the invention provides that all of the inner elements of the non-return valve are made of a synthetic plastic material. A suitable synthetic plastic material, to which preference is given for use, is an inert material that does not react to the specified fluid. For example, it is possible to use a stiffer variant of the same synthetic plastic material from which the connecting tubes and the main line are made.

The preferred distribution format of the container arrangement according to the invention is a prefabricated unit. In order to save space and for easier storability, it is preferably provided that the flexible disposable bags are evacuated. As a result, they occupy hardly more space than a film and can be easily stacked.

The prefabrication of the connecting tubes and the main line can be carried out in different ways. Basically it is possible to manufacture the whole tubing system and, if desired, also the disposable bags in one piece. However, this feature is technically very intricate and with respect to the varying number of bags, the size of the bags, the length of the lines, the cross section of the lines, etc., not very flexible. Therefore, the prefabrication is carried out preferably by connecting the individual disposable bags and the individual flexible tube sections through tube connectors, which can be constructed, for example, as tubes, which taper off conically to a point towards their ends, or as connecting crosses with arms, preferably with three arms, which taper off conically to a point towards their ends. In such an embodiment the main line consists of a plurality of tube sections, which are connected to one another through three-armed tube connectors. In this case the third arm of the tube connectors represents a branch to a connecting tube, the other end of which is connected to the inlet opening of the disposable bag through a two-armed tube connector. If necessary, the tube connections can also be secured with tamper-proof bands or tamper-proof clamps.

Furthermore, a further development of the preferred distribution format of the container arrangement according to the invention provides that said container arrangement is surrounded by a flexible, gas-tight sleeve and was sterilized as a whole. This means in other words that after the system of tubes and disposable bags is manufactured, it is packed into a germ-proof sleeve, for example, is welded into a plastic bag. The sterilization of the entire package is performed, according to this type of packaging, for example, by heating or by radiation, for example, by gamma radiation. This procedure makes it possible to carry out the prefabrication and the packaging of the container arrangement under non-sterile conditions, a feature that drastically reduces the corresponding costs. Nevertheless, the user receives a sterile unit that has been prefabricated according to his requests. Thus, the user need only insert the prefabricated and sterile unit into his filling system and to connect to the supply container(s), from which the disposable bags are to be filled. As a result, only a single hygienically critical step remains in the user's sphere of responsibility, i.e. connecting the inventive container arrangement to the supply container(s).

In the preferred method for filling the flexible disposable bags of a container arrangement according to the invention, the disposable bags are inserted into a carrier frame positioned on an electronic scale. Each connecting tube is inserted into a controllable target pinch valve, which is assigned to the attached disposable bag; and the inlet section of the main line is connected to a supply container and is inserted into a controllable supply pinch valve. In this case all of the pinch valves are initially closed. Then the following steps are carried out:

a) opening the supply pinch valve,
b) allowing the gas, contained in the main line, to escape through the gas outlet section,
c) taring the electronic scale,
d) opening a first target pinch valve,
e) filling the assigned disposable bag and at the same time monitoring a weight display of the electronic scale until a specified fill weight is reached,
f) closing the first target pinch valve, and
g) repeating the steps c to f for all other target pinch valves and assigned disposable bags.

It should be noted that when taring the electronic scale, the priming fluid in the main line is also taken into consideration. However, owing to the inventive construction of the gas outlet section the opening of the first target pinch valve does not result, as could be expected in practice, in the priming fluid flowing into the assigned first disposable bag. Rather just the first disposable bag alone can be filled from the supply container, i.e. by way of the inlet section and the first connecting tube, assigned to the first disposable bag. Only the priming fluid contained in the inlet section and in the first connecting tube, is pushed into the first disposable bag. However, this situation does not lead to a filling error. If, for example, the filling operation of the first disposable bag is stopped by closing the first target pinch valve at the instant that the display of the electronic scale shows the specified fill weight, then the priming fluid, which is pushed into the first disposable bag, from the inlet section and the first connecting tube, is replaced by the last conveyed supply fluid and contributes to the weight resting on the electronic scale. As a result, the displayed fill weight corresponds exactly to the weight of the fluid filled into the bag. The same applies to the subsequent filling of the rest of the disposable bags, where this filling operation is carried out mutatis mutandis according to the same process steps.

It should be noted that the concept "taring of the electronic scale" is to be construed herein in a broad sense and includes both the actual zero setting at a specified base load of the weighing platform as well as a computational taring, where a current display value that is different from zero is stored; and this display value has to be subtracted from the value shown by the display in order to determine the fill weight.

The term "display" is also to be construed herein in a broad sense and, in particular, is not limited to a visual plain text display. Rather the term also includes the output of electronic data for subsequent use in an electronic control unit without involving any additional manual working steps.

Moreover, a fully automatic execution of the method is the preferred embodiment. In this case the provision and setting up of a corresponding control unit as well as its effective connections to the active elements can be easily carried out by the person skilled in the art in light of the disclosure herein.

The container arrangement according to the invention is positioned advantageously in the carrier frame in such a way that the gas outlet section is positioned in close proximity to or at the highest point of the container arrangement. During this positioning, the invention can unfold its effect with the greatest possible impact.

Additional features and advantages of the invention will be apparent from the following specific description and the drawings.

BRIEF DESCRIPTION OF THE DRAWINGS

The drawings show in
FIG. 1: a schematic cross sectional representation of a container arrangement according to the invention.

DETAILED DESCRIPTION OF EXEMPLARY EMBODIMENTS

FIG. 1 shows a schematic representation of a container arrangement 10 according to the invention. The container arrangement 10 has an inlet section 12 and a gas outlet section 14. A main line 16 extends between said inlet section and said gas outlet section. The connecting tubes 18a, b, c branch off from the main line to a respective disposable bag 20a, b, c. The number of branches, i.e. in particular, the number of connecting tubes 18a, b, c and the number of disposable bags 20a, b, c, is not limited to the number three that is shown herein. Rather, any plurality of branches can be realized. In this case a plurality of branches is known under the umbrella term "manifold" in the technical jargon.

In the illustrated embodiment the inlet section 12 consists in essence of two components: in particular, a flexible inlet tube 122 and a sterile connector 124, which is connected to the flexible inlet tube at the input end. The sterile connector 124 serves to couple the inlet tube 122 to one or more supply containers 40, from which a fluid is to be filled into the disposable bags 20a, b, c. The coupling can be achieved directly or indirectly, for example, with a pump device. The specific configuration of the sterile connector 124 is of no importance for the present invention; the person skilled in the art is aware of various kinds of sterile connectors 124. For the present invention it is not absolutely mandatory, although quite advantageous, if the inlet section 12 has a sterile connector 124. Simpler embodiments of the invention can also have a conventional tube connector, a simple tube plug or just the unclosed inlet tube 122.

The inlet section 12 is connected to the main line 16 such that it conducts fluid. This main line in the illustrated embodiment is made up of a plurality of three-armed tube connectors 164 and between them the main line tubes 162. In the illustrated embodiment the main line 16 extends in essence straight. However, this feature is of no importance for the present invention. Rather the object of the main line 16 is to form a continuous connection between the inlet section 12, which is connected to the main line at the input end, and the gas outlet section 14, which is connected to the main line at the output end. Another object of the main line 16 is to provide branching points for connecting the connecting tubes 18a, b, c. The illustrated embodiment, in which three-armed tube connectors 164 and main line tubes 162 alternate, is especially advantageous with respect to a low-resistance fluid flow. However, embodiments with more than three-armed tube connectors or branches that are created by material bonding can also be implemented.

In the illustrated embodiment, a connecting tube 18a, b, c branches off at each branch, which is realized in each instance by a tube connector 164 having three arms. Each connecting tube 18a, b, c is connected to the assigned disposable bag 20a, b, c, of which only one section is shown in FIG. 1, through a tube connector 22a, b, c having two arms. Instead of the coupling through the tube connectors 22a, b, c, a material-formed coupling is also possible.

A gas outlet section 14 is connected to the main line 16 at the output end. This gas outlet section comprises an outlet tube 142, which is connected to a termination module 143 at the output end. The termination module 143 comprises in essence two functional elements: in particular, a sterile filter 144 and a non-return valve 146, which is positioned upstream of said sterile filter. In the illustrated embodiment the non-return valve 146 comprises a spherical valve body 147, which in the case of a negative pressure in the main line 16 rests sealingly against a valve seat 148. In the case of a positive pressure in the main line 16, the valve body 147 can move downstream and release the valve passage. As an alternative, the non-return valve 146 could also be constructed as a membrane valve. Furthermore, it is not absolutely mandatory that the non-return valve 146 be arranged, as shown in FIG. 1, upstream of the sterile filter 144. Rather a reverse arrangement is also possible.

In the embodiment shown in FIG. 1, all of the tube connections are secured with tube clamps 30. The necessity of this safety measure has to be weighed by the person skilled in the art in each specific case against the user's specifications and the cost of materials and assembly. For the invention per se the tube clamps 30 are not absolutely necessary.

In FIG. 1 the elements of a filling device are depicted by means of dashed lines. These elements are used preferably to fill the disposable bags 20*a, b, c*. Shown are only those elements that interact directly with the container arrangement according to the invention. They are a supply pinch valve 24, into which the supply tube 122 is inserted; the target pinch valves 26*a, b, c*, into which a connecting tube 18*a, b, c* is inserted in each case; and the storage bottoms 28*a, b, c*, of a stacking shelving system, on which the disposable bags 20*a, b, c* are stored. Additional elements of the filling device, such as, in particular, an electronic scale having a weighing platform, on which the stacking shelving system is arranged; a control unit, which actuates the scale and the pinch valves 24, 26*a, b, c* and which collects the weighing values of the electronic scale; as well as a connection to the supply container 40, if desired, including a pump, are not shown in FIG. 1. However, the general principles of such filling devices are well known to the person skilled in the art from the background art cited in the introductory part of the present application. The preferred use of the container arrangement according to the invention shall be described below. The entire container arrangement is positioned on the weighing platform of an electronic scale with or without the aid of a stacking shelf, a rack or a similar device. The sterile connector 124 of the inlet section 12 is connected to a supply container, which contains a fluid to be dispensed through, for example, a pump.

At the beginning of the process, all of the pinch valves 24, 26*a, b, c* are closed. That is, the inlet tube 122 and the connecting tubes 18*a, b, c* are pinched between the pinching jaws of the valves 24, 26*a, b, c*, so that their lumen is closed. At the beginning of the process the supply pinch valve 24 is opened, so that the line system is primed. During the priming operation, the main line 16 and the connecting tubes 18*a, b, c*, which branch off from the main line, can fill up to the respective target pinch valves 26*a, b, c*. In this case the residual gas, contained in the tubing system, is pushed through the main line 16 into the gas outlet section 16, where it passes through the non-return valve 146, which opens in the gas outlet direction, and is blown out through the sterile filter 144. Additional priming causes the priming fluid to ascend into the outlet tube 142 and even higher into the termination module 143. In this case the non-return valve 146 can be traversed by the priming fluid, but the fluid-tight sterile filter 144 cannot be traversed.

An end of the priming step can be introduced in different ways. Either a sensor, which is not shown in FIG. 1, determines a specified maximum fill level. As an alternative, an increase in pressure in the main line 16, the inlet section 12 or an upstream line section can be determined. The pressure increase would come about, if a pump pushes the priming fluid against the blocking sterile filter 144. The maximum fill level of the priming fluid is adjusted preferably in such a way that the non-return valve 146 is vented, but the sterile filter 144 is not wetted. However, it is also possible to set the maximum priming fill level below the non-return valve 146. In embodiments in which the non-return valve 146 is found upstream of the sterile filter 144, the position of the sterile filter 144 represents the maximum possible fill height; and in this case the non-return valve 146 cannot be vented.

At the end of the priming step the electronic scale is tared. That is, during the subsequent weighing processes the weight of the priming fluid is not taken into account. In other words, during the subsequent weighing processes only the increase in weight of the whole system beyond the weight of the system containing the priming fluid is determined.

For the subsequent actual filling step, a target pinch valve, for example, the target pinch valve 26*a* that is found at the very bottom in FIG. 1 has to be opened. At this stage the pressure of the liquid column in the main line 16 causes the priming fluid to be pushed out of the main line 16 through the connecting tube 18*a* into the disposable bag 20*a*. However, this process is prevented by the non-return valve 146, which closes and prevents a discharge when the sinking of the liquid column produces a negative pressure in the main line 16. Instead, fresh fluid from the supply container 40 can be pumped through the inlet tube 122 into the connecting tube 18*a* and the disposable bag 20*a*. The weight increase is recorded by the electronic scale. Due to the fact that the fill level in the main line 16 does not change owing to the non-return valve 146, the measured weight increase is exactly equal to the amount that is filled into the disposable bag 20*a*. After reaching the desired fill level, a feature that can be determined, for example, by monitoring a display of the electronic scale, the target pinch valve 26*a* is closed. With the opening of the subsequent target pinch valve 26*b*, the filling operation of the disposable bag 20*b* is initiated; and this filling operation is carried out in essentially the same way as for the disposable bag 20*a*.

By repeating the process, all of the disposable bags 20*a, b, c* can be filled one after the other.

Preferably all of the components that are associated with the container arrangement 10, i.e. all of the components that are shown in FIG. 1 with the exception of the valves 24, 26*a, b, c* that are associated with the filling device, and the shelving bottoms 28*a, b, c*, can be delivered as a prefabricated, pre-sterilized unit. During fabrication of the unit, the customer's requests with respect to the length and diameter of the tubes, number of branches, size of bag, etc. can be considered in detail. After fabrication, the entire unit is packed, preferably welded, into a germ-proof foil and sterilized using heat or radiation, for example, gamma radiation. Such commercial units have a long shelf life, can be stored in a space-saving manner, and are easy to use in suitable filling devices without running the risk of contamination.

The embodiments that are discussed in the specific description and shown in the FIGURE are only illustrative exemplary embodiments of the present invention. In light of the disclosure herein, the person skilled in the art is provided with a broad spectrum of possible design variations. In particular, the container arrangement can be constructed in a different way than shown in FIG. 1, where it is constructed of individual elements, so that the container arrangement can be constructed in essence in one piece or by material bonding.

In other words, the above description of various embodiments has been given by way of example. From the disclosure given, those skilled in the art will not only understand the present invention and its attendant advantages, but will also find apparent various changes and modifications to the structures and methods disclosed. The applicant seeks, therefore, to cover all such changes and modifications as fall within the spirit and scope of the invention, as defined by the appended claims, and equivalents thereof.

The invention claimed is:

1. A container arrangement, comprising:
   a flexible common main line central section extending from an input end to an output end,
   a plurality of flexible disposable bags, each of which has an inlet element to which a plurality of flexible connecting tubes are respectively attached, wherein each of the connecting tubes branches off from the flexible common main line central section,
   a common inlet section connected at the input end of the common main line central section, and
   a common gas outlet section connected at the output end of the common main line central section and defining a gas outlet direction,
   wherein a non-return valve, which is configured to close against the gas outlet direction, and a gas permeable, liquid-impermeable sterile filter are arranged in the common gas outlet section.

2. The container arrangement as claimed in claim 1, wherein
   the non-return valve and the sterile filter are disposed in a common housing.

3. The container arrangement as claimed in claim 1, wherein the non-return valve is arranged downstream of the sterile filter in the gas outlet direction and is constructed as a gas valve.

4. The container arrangement, as claimed in claim 1, wherein the non-return valve is arranged upstream of the sterile filter in the gas outlet direction and is constructed as a fluid valve.

5. The container arrangement as claimed in claim 4, wherein all inner elements of the non-return valve are made of plastic.

6. The container arrangement as claimed in claim 1, wherein the flexible disposable bags are evacuated.

7. The container arrangement as claimed in claim 1, wherein at least the connecting tubes, the common main line central section, the common inlet section, and the common gas outlet section are sterilized as a unit and surrounded by a flexible, gas-tight sleeve.

8. A method for filling the flexible disposable bags of the container arrangement as claimed in claim 1, wherein the disposable bags are inserted into a carrier frame positioned on an electronic scale, each connecting tube is inserted into a controllable target pinch valve to which a respective disposable bag is assigned, and the inlet section is connected to a supply container and inserted into a controllable supply pinch valve, and wherein all of the pinch valves are initially closed, comprising:
   a) opening the supply pinch valve,
   b) allowing the gas contained in the main line to escape through the gas outlet section,
   c) taring the electronic scale,
   d) opening a first target pinch valve,
   e) filling the assigned disposable bag and contemporaneously monitoring a weight display of the electronic scale,
   f) closing the first target pinch valve upon reaching a specified fill weight,
   g) repeating the steps c through f for all other target pinch valves and respective assigned disposable bags.

9. The method as claimed in claim 8, wherein the gas outlet section is positioned closer to a highest point of the container arrangement than are remaining sections of the container arrangement.

10. A container arrangement, comprising:
    a flexible common main line central section extending from an input end of the common main line central section to an output end of the common main line central section,
    a plurality of inlet elements configured to sealingly attach to a plurality of respective flexible disposable bags,
    a plurality of flexible connecting tubes sealingly interconnecting the common main line central section with each of the inlet elements,
    a common inlet section connected at the input end of the common main line central section, and
    a common gas outlet section connected at the output end of the common main line central section and defining a gas outlet direction,
    wherein the gas outlet section comprises a non-return valve, which closes against the gas outlet direction, and a gas permeable, liquid-impermeable sterile filter.

11. The container arrangement as claimed in claim 1, wherein the non-return valve is configured to close against the gas outlet direction to at least one of liquid or gas, and to open in the outlet direction to at least one of liquid or gas.

12. The container arrangement as claimed in claim 1, wherein no non-return valves or sterile filters are arranged other than in the common gas outlet section.

13. The container arrangement as claimed in claim 10, wherein the non-return valve is configured to close against the gas outlet direction to at least one of liquid or gas, and to open in the outlet direction to at least one of liquid or gas.

14. The container arrangement as claimed in claim 1, wherein no non-return valves or sterile filters are arranged other than in the common gas outlet section.

* * * * *